United States Patent [19]

Zhong et al.

[11] Patent Number: 5,320,961

[45] Date of Patent: Jun. 14, 1994

[54] METHOD FOR ASEXUAL IN VITRO PROPAGATION OF FERTILE CORN PLANTS

[75] Inventors: Heng Zhong, East Lansing; Masomeh B. Sticklen, Okemos; Chinnathambi Srinivasan, East Lansing, all of Mich.

[73] Assignee: Board of Trustees operating Michigan State University, East Lansing, Mich.

[21] Appl. No.: 977,253

[22] Filed: Nov. 16, 1992

[51] Int. Cl.$^5$ .............................................. C12N 5/00
[52] U.S. Cl. ........................... 435/240.45; 435/240.1; 435/240.4; 435/240.48; 435/240.49
[58] Field of Search ................... 435/240.49, 240.54, 435/240.4, 240.1

[56] References Cited

U.S. PATENT DOCUMENTS

| H951 | 8/1991 | Simpson | 435/240.4 |
|---|---|---|---|
| 4,665,030 | 5/1987 | Close | 435/240.54 |
| 4,666,844 | 5/1987 | Cheng | 435/240.54 |
| 4,762,790 | 8/1988 | Whitten | 435/240.45 |
| 4,806,483 | 2/1989 | Wang | 435/240.49 |
| 4,830,966 | 5/1989 | Close | 435/240.49 |
| 4,843,005 | 6/1989 | Cheng et al. | 435/240.49 |
| 4,857,465 | 8/1989 | Barwale et al. | 435/240.49 |
| 5,164,310 | 11/1992 | Smith et al. | 435/172.3 |
| 5,281,529 | 1/1994 | Zheng et al. | 435/240.45 |

FOREIGN PATENT DOCUMENTS 2099851 12/1982 United Kingdom .

OTHER PUBLICATIONS

Bhaskaran, S., and Smith, R. H. Crop Sci. 30, 1328–1336 (1990).
Vasil, I. K., J. Plant Physiol. 128, 193–218 (1987).
Zhong, H.; et al., Planta vol. 187, No. 4, Jul. 1992, pp. 483–489.
Green, C. E.; et al., Crop Science vol. 15, No. 1, Jan.-Feb. 1975, pp. 417–421.
Ed. D. A. Evans, et al., *Handbook of Plant Cell Culture*, vol. 1, Macmillan Publishing Co., 1983 pp. 177–227, Chap. 5.
Itisajima, S.,–*Plant Tissue Culture* 1982.-Ed. Akio Fujiwara, pp. 141–142.
Fosket, D. E., *Plant Growth Substances*, Ed. F. Skoog, Springer-Verlag, Berlin Publisher, 1979, pp. 362–369.
Vasil, I. K., *Plant Tissue Culture* 1982, Ed. A. Fujiwara, pp. 101–104.
Chang, Y. F., "Plant Cell Reports," vol. 2, 1983, pp. 183–185.
Vasil, I. K., et al., *International Review of Cytology*, Suppl. 11A, Chap. 6, 1980, pp. 145–173.
Hodges, T. K., et al., "Biotechnology," vol. 4, Mar. 1986, pp. 219–223.
A. Wang, "Plant Cell Rep.," vol. 6, 1987, pp. 360–362.
Raman, K., et al., "Ann. Bot." vol. 45, 1980, pp. 183–189.
Vasil, I. K., Biotechnology 8, 296–301 (1990).
Potrykus, I., Physiol. Plant, 79, 125–134 (1990).
Rhodes, C. A., Pierce, D. A., Mettler, L. J., Mascarenhas, D., and Detmer, J. J. Science 240, 204–207 (1988).
Fromm, M. E., Morrish, F., Armstrong, C., Williams, R., Thomas, J., Klein, T. M., Biotechnology 8, 833–839 (1990).
Gordon-Kamm, W. J., Spencer T. M., Manganno, M. L., Adams, T. R., Daines, R. J., Willets, N. G. Rice, T. B., Mackey, C. J., Kruger, R. W., Kaush, A. P., Lamaux, P. G., Plant Cell 2, 603–608 (1990).
Springer, W. D., Green, C. E., Kohn, K. A., Protoplasma 101, 269–281 (1979).
Vasil, V., Lu, C., Vasil, I. K. Protoplasma 127, 1–8 (1985).
Duncan, D. R., Williams, M. E., Zehr, B. E., Widholm, J. M., Planta 165, 322–332 (1985).
Rhodes, C. R., Green, C. E., Phillips, R. L., Plant Sci 46, 225–232 (1986).
Conger, B. V., Novak, F. J., Afza, R., Erdelsky, K., Plant Cell Rep. 6, 345–347 (1987).
Murashige, T., Skoog, F., Physiol. Plant. 15, 473–497 (1962).
McDaniel, C. N., and Poethig, R. S., Planta 175, 13–22 (1988).

*Primary Examiner*—Douglas W. Robinson
*Assistant Examiner*—Kristin Larson
*Attorney, Agent, or Firm*—Ian C. McLeod

[57] ABSTRACT

A method for asexual in vitro propagation of corn plants is described. The plant tissue (shoot tips or apices) are differentiated with 2,4-dichlorophenoxy acetic acid (2,4-D) and $N^6$-benzyladenine (BA) and mixtures thereof and then the differentiated tissue is grown in indole-3-butyric acid (IBA) to produce the corn plant which is fertile.

5 Claims, 4 Drawing Sheets

METHOD FOR ASEXUAL IN VITRO PROPAGATION OF FERTILE CORN PLANTS

BACKGROUND OF THE INVENTION

(1) Field of the Invention

The present invention relates to an in vitro method for asexually propagating corn plants in vitro into a fertile corn plant. In particular the present invention relates to the use of 2,4-dichlorophenoxyacetic acid (2,4-D) or $N^6$-benzyladenine (BA) and mixtures thereof to produce differentiated corn tissue from shoot tips or apices and then growing the differentiated tissue in indole-3-butyric acid (IBA) composition to produce the corn plant.

(2) Prior Art

An efficient and reproducible in vitro technique permitting the production of whole plants from transformed cells is an integral part of successful genetic engineering of plants (Vasil, I. K., BioTechnology 8, 296-31 (1990); and Potrykus, I., Physiol. Plant. 79, 125-134 (1990)). Currently, immature zygotic embryos are the most reliable explant source to develop regeneratively-competent calli, cell suspensions and protoplasts for transformation of corn (Rhodes, C. A., Pierce, D. A., Mettler, L. J., Mascarenhas, D., and Detmer, J. J., Science 240, 204-207 (1988); Fromm, M. E., Morrish, F., Armstrong, C., Williams, R., Thomas, J., Klein, T. M., BioTechnology 8, 833-839 (1990); and Gordon-Kamm, W. J., Spencer T. M., Manganno, M. L., Adams, T. R., Daines, R. J., Willets, N. G., Rice, T. B., Mackey, C. J., Krueger, R. W., Kaush, A. P., Lamaux, P. G., Plant Cell 2,603-608 (1990)).

Plant regeneration through somatic embryogenesis has been routinely achieved in Zea mostly from in vitro cultures of 1-2 mm long immature zygotic embryos excised precisely 10-15 days after fertilization (Springer, W. D., Green, C. E., Kohn, K. A., Protoplasma 101, 269-281 (1979); Vasil, V., Lu, C., Vasil, I. K., Protoplasma 127, 1-8 (1985); Duncan, D. R , Williams, M. E., Zehr, B. E., Widholm, J. M , Planta 165,322-332 (1985); Hodges, T. K., Kamo, K. K., Imbrie, C. W., Becwar, M. R., BioTechnology 4, 219-223 (1986)). Cultures of tassel primordia (Rhodes, C. R., Green, C. E., Phillips, R. L., Plant Sci 46, 225-232 (1986)), mature seed embryos (Wang, A., Plant Cell Rep. 6, 360-362 (1987)), and leaf segments (Conger, B. V., Novak, F. J., Afza, R., Erdelsky, K., Plant Cell Rep. 6, 345-347 (1987)) of corn have also regenerated plants through somatic embryogenesis.

What is needed is a method for producing mature corn plants using an asexual, genotype-independent reproduction, wherein the plants are fertile.

OBJECTS

It is therefore an object of the present invention to provide a method for the asexual, genotype-independent reproduction of corn plants which are fertile. Further, it is an object of the present invention to provide a method which is relatively simple and economical. These and other objects will become increasingly apparent by reference to the following description and the drawings.

GENERAL DESCRIPTION

The present invention relates to a method for asexually propagating corn plant tissue in vitro to produce a fertile corn plant which comprises providing immature corn shoot tip or apices plant tissue in a first growth medium containing a first growth promoting compound selected from the group consisting of a cytokinin and mixtures of the auxin and cytokinin and an amino acid source at a concentration which promotes differentiated tissue in the form of multiple shoot formation, calli proliferation or somatic embryos of the plant tissue over a period of time; and growing the differentiated tissue in a second growth medium in the presence of a second growth promoting compound selected from the group consisting of an auxin and a mixture of auxin with a cytokinin over a period of time to produce the corn plant.

The auxins which are particularly useful are 3,6-dichloro-o-anisic acid (dicamba); 2,4-dichlorophenoxyacetic acid (2,4-D); indole-3-acetic acid (IAA); indole-3-butyric acid (IBA); and α-naphthaleneacetic acid (NAA). The cytokinins are particularly 6-benzylaminopurine (or 6-benzyladenine) (BAP (or BA));

6-furfurylaminopurine (Kinetin); and 6-(4-hydroxy-3-methylbut-2-enylamino)purine (Zeatin). The first growth promoting compound is used in an amount between about 4 and 9 $\mu$M. The 2,4-D is used in an amount between about 0.001 and 2.25 $\mu$M. The BA is present in the second growth promoting compound in an amount between 2,25 and 9.0 $\mu$M.

The present invention further relates to a method for asexually propagating corn plant tissue in vitro to produce a fertile corn plant which comprises: providing immature corn shoot tip or apices plant tissue in a first growth medium containing a first growth promoting compound selected from the group consisting of $N^6$-benzyladenine (BA) and mixtures of 2,4-dichlorophenoxy acetic acid (2,4-D) and the BA and an amino acid source at a concentration which promotes differentiated tissue in the form of multiple shoot formation, calli proliferation or somatic embryos of the plant tissue over a period of time; and growing the differentiated tissue in a second growth medium in the presence of a second growth promoting compound selected from the group consisting of indole-3-butyric acid (IBA) alone and mixtures with BA thereof over a period of time to produce the corn plant.

In vitro methods to regenerate clumps of multiple shoots and somatic embryos at high frequency were developed from shoot tips of aseptically-grown seedlings as well as from shoot apices of precociously-germinated immature zygotic embryos of corn (Zea mays L.). About 500 shoots were produced from a shoot tip after eight weeks of culture (primary culture and one subculture of four weeks) in darkness on Murashige and Skoog basal medium (MS) supplemented with 500 mg/L casein hydrolysate (CH) and 9 $\mu$M $N^6$-benzyladenine (BA). In this medium, shoots formed in shoot tips as tightly packed "multiple shoot clumps" (MSC), which were composed of some axillary shoots and many adventitious shoots. When the shoot tips were cultured on MS medium containing 500 mg/L CH, 9 $\mu$M BA and 2.25 $\mu$M 2,4-dichlorophenoxyacetic acid (2,4-D), most of the shoots in the clumps were adventitious in origin. Similar shoot tips cultured on MS medium containing 500 mg/L CH, 4.5 $\mu$M BA and 2.25 $\mu$M 2,4-D regenerated many somatic embryos within eight weeks of culture. Somatic embryos were produced either directly from the shoot apical meristems or from calli derived from the shoot apices. Both the MSC and the embryos produced normal shoots on MS medium containing 2.25 $\mu$M BA and 1.8 $\mu$M indole-3-butyric acid (IBA). These shoots were rooted on MS medium containing 3.6 $\mu$M IBA, and fertile corn plants were grown in the greenhouse. The sweet-corn genotype, Honey N Pearl, was used for the experiments described above, but shoot-tip cultures from all of 19 other corn genotypes tested also formed MSC on MS medium containing 500 mg/L CH and 9 $\mu$M BA.

SPECIFIC DESCRIPTION

In attempting to identify an alternative and highly-regenerative explant source, several in vitro procedures were developed that permit one to obtain high frequency differentiation of adventitious shoots and somatic embryos in corn-shoot tips excised from seedlings grown in vitro.

MATERIALS AND METHODS

Mature seeds (caryopses, kernels), of twenty corn (Zea mays L.) genotypes listed in Table 1 were used for this research. Corn seeds were surface-sterilized first in 70% ethanol for 10 minutes, washed once with sterile water and then soaked for 30 minutes in 2.6% sodium hypochlorite (prepared from commercial bleach) containing 0.1% Tween 20 (polyoxyethylene sorbitan monolaurate). The surface-sterilized seeds were washed three times with sterile distilled water and germinated aseptically on Murashige and Skoog (Murashige, T., Skook, F., Physiol. Plant. 15, 473–497 (1962) basal medium (MS-M5519) containing:

| | |
|---|---|
| Ammonium Nitrate | 1650.0 |
| Boric Acid | 6.2 |
| Calcium Chloride (Anhydrous)* | 332.2 |
| Cobalt Chloride-6H$_2$O | 0.025 |
| Cupric Sulfate-5H$_2$O | 0.025 |
| Na$_2$—EDTA | 37.26 |
| Ferrous Sulfate-7H$_2$O | 27.8 |
| Magnesium Sulfate(Anhydrous)** | 180.7 |
| Manganese Sulfate-H$_2$O*** | 16.9 |
| Molybdic Acid (Sodium salt)-2H$_2$O | 0.25 |
| Potassium Iodide | 0.83 |
| Potassium Nitrate | 1900.0 |
| Potassium Phosphate Monobasic | 170.0 |
| Zinc Sulfate-7H$_2$O | 8.6 |
| Glycine (free base) | 2.0 |
| Myo-Inositol | 100.0 |
| Nicotinic Acid (free acid) | 0.5 |
| Pyridoxine HCl | 0.5 |
| Thiamine-HCl | 0.1 |
| Grams of powder to prepare 1 liter | 4.4 |

*Original formula contains calcium chloride dihydrate at 440.0 mg/L.
**Original formula contains magnesium sulfate heptahydrate at 370.0 mg/L.
***Original formula contains manganese sulfate tetrahydrate at 22.30 mg/L.

in Petri dishes (100 mm diameter, 15 mm deep). Seedlings grew about 3–5 cm long within a week of sowing the seeds. The position of the shoot tip inside the covering leaf sheath of the seedling could be determined by the localized enlargement of the seedling at the junction of the mesocotyl and the leaf sheath. About 5 mm long sections of seedlings containing a shoot tip, three to five leaf primordia, and a portion of young leaf and stem immediately below the leaf primordia were excised and cultured on MS basal medium supplemented with 500 mg/L enzymatic casein hydrolysate (CH) and various concentrations of $N^6$-benzyladenine (BA; 2.25, 4.5, 9, or 18 $\mu$M). The pH of the media was adjusted to 5.8 with 0.1 N sodium hydroxide, and the media were solidified with 7 g/L Phytagar (Gibco Labs, Grand Island, N.Y., USA). Three shoot tips were cultured in each Petri dish on 20 ml of medium. The explants were laid horizontally and partly buried in the medium. Four weeks later, the multiple shoot clumps arising from these explants were divided and subcultured on MS basal medium containing 500 mg/L CH and 9 $\mu$M BA. Subsequent subcultures were also done at four week intervals. All cultures were incubated at 25° to 27° C. in darkness.

Shoot-multiplication cultures were also established from immature embryos of the sweet-corn cultivar, Honey N Pearl. Corn plants were first grown in a greenhouse at 27° C., and open-pollinated ears were collected about 10–15 days after pollination. These immature ears were surface sterilized with 0.5% sodium hypochlorite for 10 minutes and rinsed three times with sterile distilled water. Immature embryos (1–3 mm long) were extracted from the kernels and cultured on MS basal medium supplemented with CH and the same concentrations of BA as used for shoot-tip cultures.

To induce adventitious shoot formation and/or somatic embryogenesis, shoot-tip explants from one week old, in vitro germinated seedlings or shoot-tip cultures from four week old multiple shoot clumps developed on MS basal medium containing 500 mg/L CH and 9 μM BA, were transferred to MS basal medium containing 500 mg/L CH, 2.25 μM 2,4-D and 4.5, 9 or 18 μM BA and agar. Each of these cultures were subcultured once on the same medium after four weeks.

To test the regenerative response of different corn genotypes, 50 shoot-tip explants from seedlings of each of the genotypes listed in Table 1 were cultured on MS basal medium supplemented with various concentrations of BA (2.25, 4.5, 9, 18 μM) with or without 2,4-D (2.25 μM). The cultures were visually scored at the end of eight weeks to estimate the relative efficiency of multiple shoot formation.

TABLE 1

Relative efficiency of shoot multiplication seedling shoot-tip cultures of corn genotypes. The cultures were evaluated following eight weeks of continuous culture on agar-solidified MS basal medium supplemented with 500 mg/L CH and different concentrations of BA with or without 2,4-D and incubated at 25-27° C. in darkness.
Number of shoots per shoot tip culture $-$ = <10, + = 10-20, ++ = 20-50, +++ = >50.

| | Growth regulator concentration (μM) | | | | | | |
|---|---|---|---|---|---|---|---|
| 2,4-D | 0 | 0 | 0 | 0 | 2.25 | 2.25 | 2.25 |
| BA | 2.25 | 4.5 | 9.0 | 18.0 | 4.5 | 9.0 | 18.0 |
| Sweet corn genotypes[a] | | | | | | | |
| EXP 4427 | − | + | ++ | − | +++ | +++ | +++ |
| Honey N Pearl | + | ++ | +++ | + | ++ | +++ | +++ |
| Illinois Gold | + | ++ | ++ | ++ | +++ | +++ | +++ |
| Xtra Sweet | | | | | | | |
| Michigan genotypes[b] | | | | | | | |
| 509 | − | + | ++ | + | ++ | ++ | ++ |
| 420 | − | + | + | − | − | ++ | − |
| 5922 | − | + | + | − | − | ++ | +++ |
| 582 | − | + | + | + | ++ | ++ | ++ |
| 579 | − | − | + | − | ++ | ++ | ++ |
| 482 | + | ++ | ++ | ++ | +++ | +++ | +++ |
| 466 | − | + | + | ++ | ++ | ++ | ++ |
| Illinois genotypes[a] | | | | | | | |
| B73 | − | + | + | + | +++ | +++ | + |
| M79 | + | + | + | − | ++ | ++ | ++ |
| VA99 | − | + | + | − | +++ | ++ | ++ |
| CM105 | − | + | + | − | − | ++ | − |
| B84 | − | − | + | − | + | + | − |
| PA | − | + | + | + | ++ | − | − |
| FR634 | − | + | + | − | ++ | + | − |
| FR632 | − | − | + | − | + | ++ | ++ |
| FRM017 | + | + | + | + | ++ | ++ | − |
| Minnesota genotype[c] | | | | | | | |
| A188 | − | + | + | − | − | − | ++ |

Seeds were obtained from
[a]Illinois Foundation Seeds, Inc., Champaign, IL., USA.
[b]Michigan Agricultural Experiment Station, East Lansing, MI, USA.
[c]Crop Breeding Project, Dept. of Agronomy, University of Minnesota, St. Paul, MO., USA.

Samples of shoot and somatic embryogenic cultures were fixed in 3% glutaraldehyde, dehydrated in an ethanol series, critical point dried, and coated with gold. Scanning electron micrographs were obtained with a JEOL (Tokyo, Japan) JSM 31scanning electron microscope.

Green corn shoots were obtained from the dark-grown multiple shoot clumps and from embryogenic cultures after transfer to MS basal medium containing 500 mg/L CH, 2.25 μM BA, and 1.8 μM indole-3-butyric acid (IBA) and exposure to continuous light (60 μE. $m^{-2}·s^{-1}$ from cool white 40W Econ-o-watt fluorescent lamp, Philips Westinghouse, USA). Corn plantlets were rooted in Magenta GA 7 vessels (65 mm; 65 mm; 100 mm; Magenta Corp., Chicago, Ill., USA) containing 50 ml MS basal medium supplemented with 3.6 μM IBA and agar. Mature corn plants were obtained after transplanting these rooted plantlets into a soil mixture composed of 1:1 (v/v) peat and perlite and fertilizing weekly with Peters 20:20:20 fertilizer (W. R. Grace & Co., Cambridge, Mass., USA).

Figure 1:
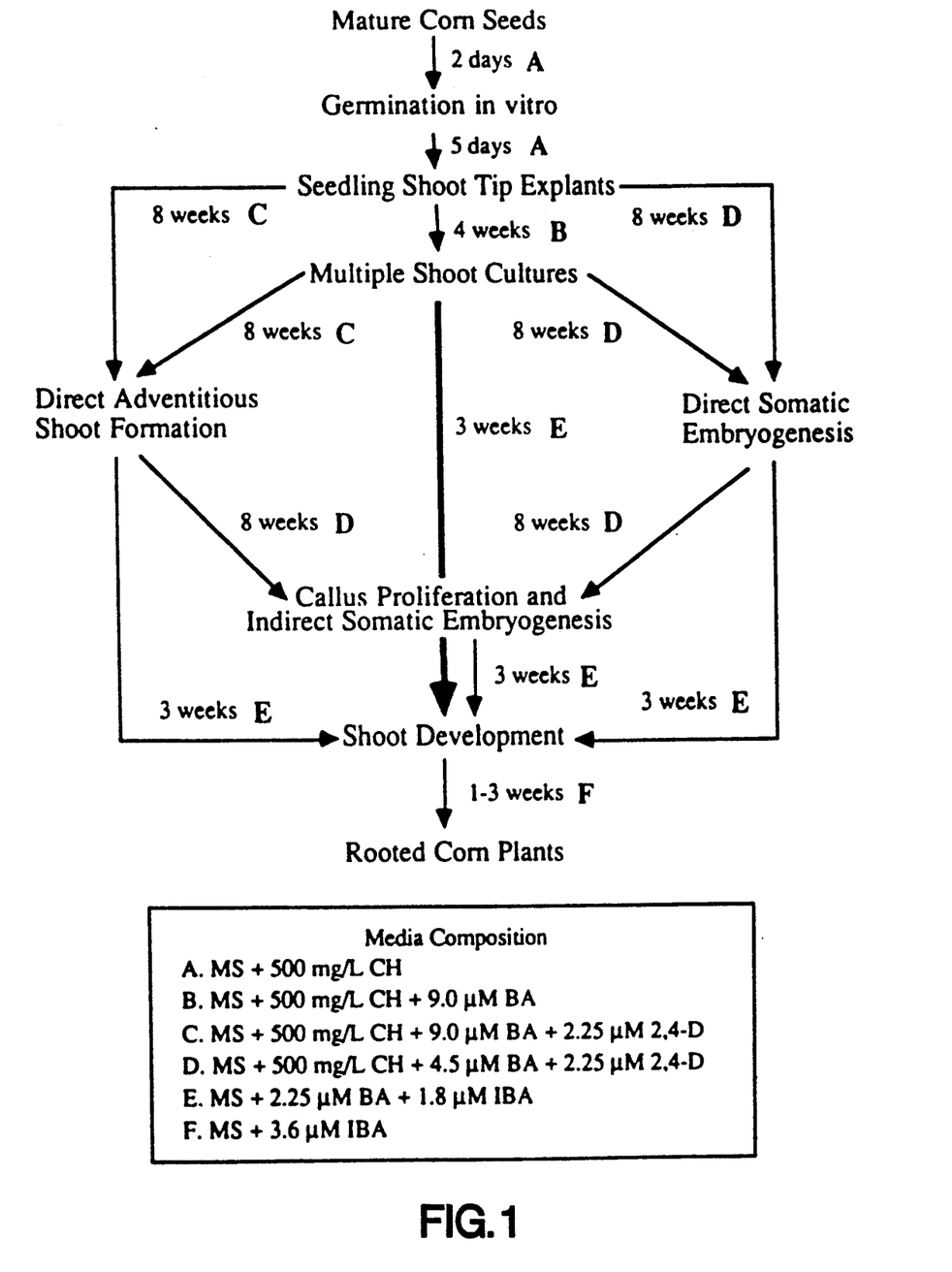
FIG. 1 is a chart showing the morphogenic pathways in corn shoot-tip cultures incubated on MS medium containing various concentrations of growth regulators.

All chemicals used in this research including the MS basal medium were obtained from Sigma Chemical Co., St. Louis, Mo., USA. RESULTS The morphogenic pathways of corn-seedling shoot tips cultured on MS media containing BA and 2,4-D are summarized in a flow diagram (FIG. 1).

Shoot-multiplication cultures. Preliminary experiments showed that shoot tips excised from seedlings of any age, as well as tips from the terminal and axillary shoots of greenhouse-grown corn plants, all produced multiple shoot clumps (MSC) in the shoot-multiplication medium (data not shown). For the experiments reported here sections of one week old corn seedlings containing shoot tips were used as explants primarily because the position of the shoot tip in the seedlings can easily be recognized by a localized visible enlargement.

Figure 2:
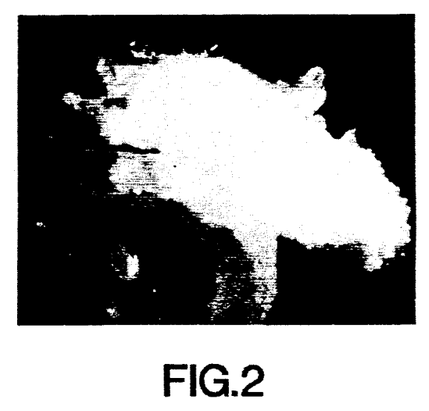
FIG. 2 is a photograph showing the formation of multiple shoots from a shoot-tip explant two weeks after culture on CSM. X 11.
Figure 3:
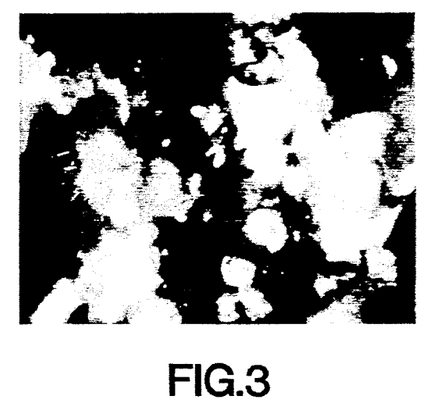
FIG. 3 is a photograph showing a multiple shoot clump four weeks after culture on CSM. ×20.
Figure 4:
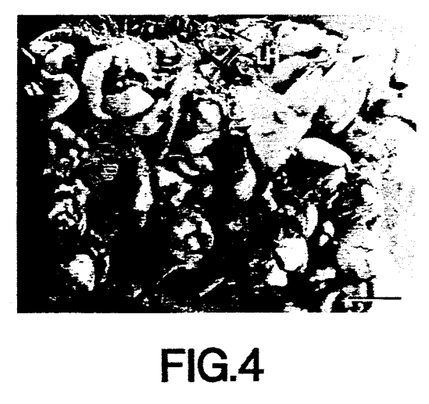
FIG. 4 is a photograph showing a scanning electron micrograph of a section of MSC four weeks after incubation in darkness on CSM. L, leaf; LH, leaf hair; ST, shoot tip. Bar=500 µm; ×20.

Shoot tips began to produce MSC within one to two weeks of culture on MS basal medium containing 500 mg/L CH and various concentrations of BA. During the initial culture, shoot multiplication from shoot tips occurred inside the leaves, and therefore, the shoot clumps were not visible until the leaf sheath of the explants was removed (FIG. 2). Shoot multiplication was observed from shoot-tip explants on medium with each of the BA concentrations tested (2.25-18 μM), but the maximum number of normal shoots was obtained at 9 μM BA. Therefore, MS basal medium supplemented with 500 mg/L CH and 9 μM BA was designated as corn shoot-multiplication medium (CSM) (Table I). It appears that rapid activation of axillary buds with little internode elongation followed by differentiation of adventitious shoots from the shoot meristem without apparent callus formation produced the multiple shoot clumps (MSC) in each shoot tip culture (FIG. 3). Shoots multiplied as tight clusters of 0.5-2 mm long shoots each with two or three visible leaf primordia, and the number of shoots per MSC could be counted only under a binocular stereomicroscope. About 20-50 shoots were produced per shoot tip explant within four weeks of culture (FIG. 4). Each of these shoot clumps was divided into ten units, each unit containing two to five tiny shoots. These shoot-clump units were subcultured on fresh CSM every four weeks. At the end of the first subculture (about nine weeks after sowing the seeds), each seedling shoot tip had produced about 500 shoot apices.

Shoot multiplication cultures have been maintained for a year by regular division and subculture of shoot clumps onto fresh CSM every four weeks. Repeated subculture of shoot cultures onto CSM produced more compact shoot clusters because of the very high frequency of shoot initiation. Scanning electron micrographs showed the crowded shoot clumps and the formation of trichomes (hairs) on the leaves (FIG. 4). Those shoot primordia which were trapped in the middle of the crowded-shoot clumps tended to produce abnormal shoots with twisted leaves. However, these apparently abnormal shoots eventually grew into normal plants when they were transferred onto MS medium lacking BA and were exposed to light (not shown).

Multiple shoot clumps were also produced from the precociously-germinated seedling shoot apices of in vitro cultured immature zygotic embryos of Honey N Pearl when cultured on CSM. These shoot cultures also displayed similar intensity of shoot multiplication to that described for shoot tip cultures of seedlings.

Figure 5:
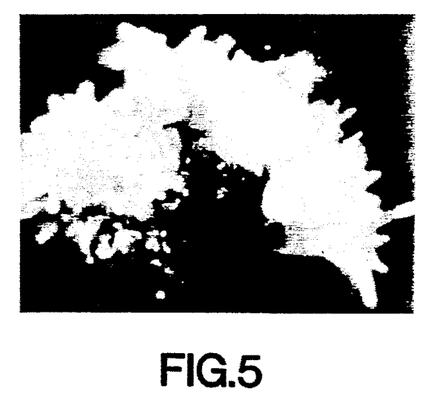
FIG. 5 is a photograph showing adventitious shoot formation from a section of MSC after eight weeks of culture on CSM supplemented with 2.25 µM 2,4-D.×16.
Figure 6:
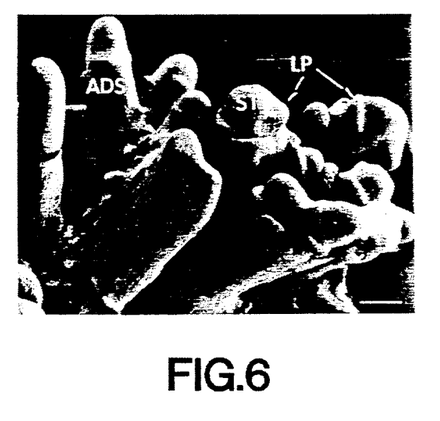
FIG. 6 is a photograph showing a scanning electron micrograph of a section of MSC shown in FIG. 5. ADS, adventitious shoot; LP, leaf primordium; ST, shoot tip Bar=200 µm;×40.

When the shoot tip explants from in vitro germinated seedlings and shoot clump units from the MSC of Honey N Pearl were transferred to CSM supplemented with 2.25 μM 2,4-D and incubated in darkness, the shoot tip enlarged and differentiated into shoot clumps containing many adventitious shoots (FIGS. 5 and 6). The number of adventitious shoots that were produced per shoot tip explant was relatively high when the culture was on a medium containing a combination of 2,4-D and BA as compared to shoot tips cultured on BA alone. Moreover, adventitious shoots that were produced in the presence of 2,4-D and BA remained smaller, and leaf elongation was minimal. There was no apparent callus formation preceding the adventitious-shoot multiplication.

Figure 7:
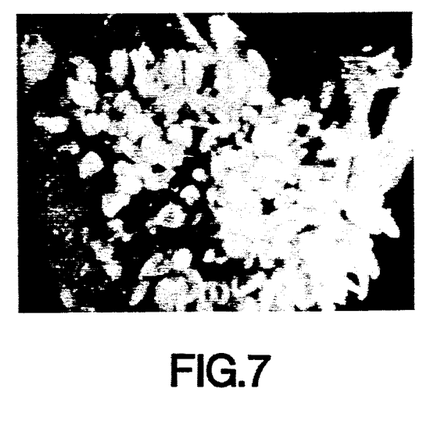
FIG. 7 is a photograph showing direct somatic embryogenesis from a shoot-tip culture eight weeks after incubation on MS medium containing 500 mg/L CH, 2.25 µM 2,4-D and 4.5 µM BA.×16.

Direct somatic embryogenesis from shoot tip cultures. Compact and organized tissue layers with a smooth epidermis were produced from each shoot tip cultured either in light or in darkness on MS medium containing 500 mg/L CH, 2.25 μM 2,4-D and 4,5 μM BA (hereafter called embryogenic medium) within about eight weeks of incubation. These organized tissue layers, which will be hereafter called "tissue stratum", differentiated into a virtual lawn of embryos (FIG. 7).

Figure 8:
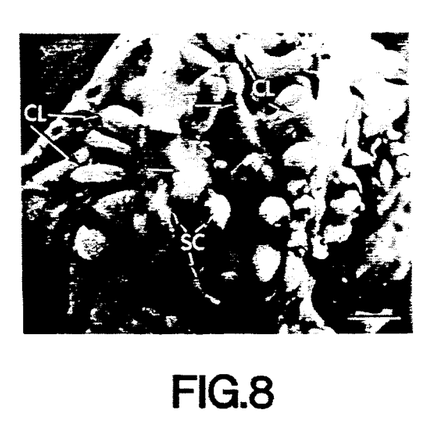
FIG. 8 is a photograph showing scanning electron micrograph of a culture showing the formation of scutella and coleoptiles from the tissue stratum. CL, coleoptile; SC, scutellum; ST, shoot tip; TS, tissue stratum. Bar=500 µm;×20.

The scutella of the embryos initiated first, and the preservation of cellular integrity of the epidermis of the tissue layer during the initiation of scutella was observed under the scanning electron microscope. Somatic embryos emerged directly from the tissue stratum without apparent callus formation (FIG. 8). The leaf-like scutella and the tubular coleoptiles differentiated at random from the sub-epidermal cells of the tissue stratum by expanding and folding without disrupting the outer layers of the tissue stratum (FIG. 8). Therefore, the scutella were spatially separated from the coleoptiles. A row of coleoptiles could be seen without the subtending scutella in the SEM. Most of the coleoptiles seems to be long and hollow structures, while a few initiated visible shoot tips (FIG. 8). The root poles of the so-called embryos were not apparent and may have been merged with the tissue stratum. The shoot tips cultured on MS medium containing 500 mg/L CH and 2.25 μM 2,4-D alone produced only non-morphogenic calli.

Figure 9:
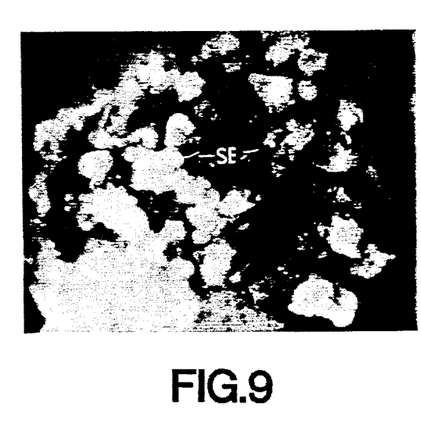
FIG. 9 is a photograph showing indirect somatic embryogenesis in callus cultures derived from a multiple shoot clump. SE, somatic embryo.×16.
Figure 10:
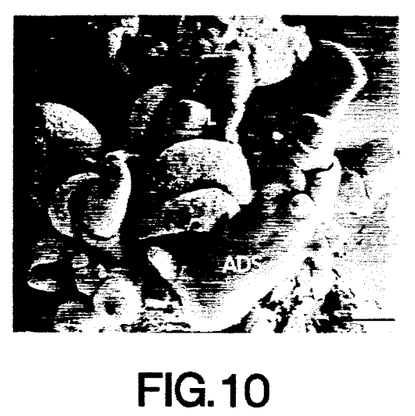
FIG. 10 is a photograph showing a scanning electron micrograph of a mixture of adventitious shoots and somatic embryos in an embryogenic culture ADS, adventitious shoot; CL, coleoptile; SC, scutellum. Bar=200 µm;×20.

Indirect somatic embryogenesis from callus cultures. When pieces of the adventitious shoot cultures and direct-embryo-forming cultures were transferred to embryogenic medium, friable calli were produced followed by somatic embryogenesis when examined eight weeks after culture. These somatic embryos turned green after one week of exposure to light (FIG. 9). Mixtures of both adventitious shoots and somatic embryos were observed in some cultures (FIG. 10).

Response of different genotypes. All 20 corn genotypes tested produced multiple shoot cultures on CSM (9 μM BA) (Table 1). Shoot tips from 18 out of 20 genotypes tested produced at least 10 shoots per tip when cultured on VSM supplemented with 2.25 μM 2,4-D. More than half of the genotypes did not respond to the lowest (2.25 μM) and the highest (18 μM) concentrations of BA. Preliminary experiments showed that 2,4-D alone failed to induce multiple-shoot formation from shoot-tip explants. In general, shoot regeneration in most genotypes was high on media containing both 2,4-D and BA. The shoots formed on media containing combinations of 2,4-D and BA may have been derived either from somatic embryos, from adventitious buds, or from both.

Figure 11:
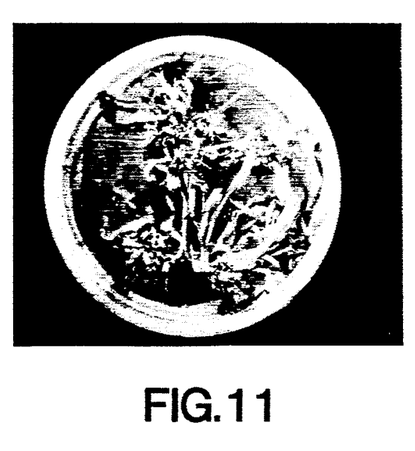
FIG. 11 is a photograph showing shoot development from MSC after transfer to MS medium containing 2.25 µM BA and 1.8 µM IBA.×0.6.
Figure 12:
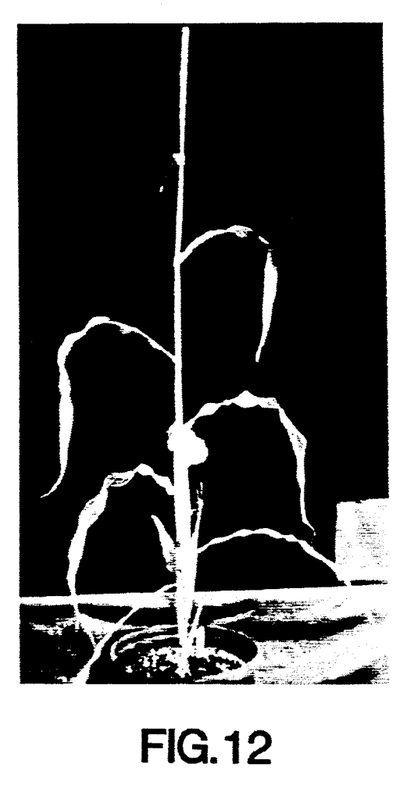
FIG. 12 is a photograph showing a fertile corn plant regenerated from a multiple shoot clump. X 0.08.

Shoot elongation and rooting. Regardless of the exact morphogenic pathway, normal shoots were formed when the shoot-multiplication cultures and embryogenic cultures were exposed to light. However, for optimum shoot elongation, shoot clusters and somatic embryos had to be transferred to MS basal medium containing 2.25 μM BA and 1.8 μM IBA (FIG. 11). When the shoots were 4 to 6 cm long with three or four leaves, they were rooted on MS basal medium containing 3.6 μM IBA. Shoot elongation and rooting did not require CH in the medium. About 80% of the shoots or somatic embryos developed into fertile plants (FIG. 12). The other regenerants from multiple shoot clumps and from the somatic embryogenic cultures did not develop into plants possibly because of the nutritional limitations imposed by the crowded shoots or embryos.

The present work showed for the first time that the corn shoot meristem can be committed to form either clumps of multiple shoots or somatic embryos in vitro by manipulating the concentration of BA and 2,4-D in the culture medium. The commitment of corn-shoot meristem to form either shoots or somatic embryos (FIGS. 2 to 10) support the concept of McDaniel and Poethig (McDaniel, C. N., and Poethig, R. S., Planta 175, 13-22 (1988)) that the organ formation from corn apical meristem cells is determined just before the organ begins to be initiated. Sorghum-shoot tips also similarly differentiated into somatic embryos in the presence of 11 µM 2,4-D and 2.25 µM kinetin, another cytokinin, while the meristems cultured on 45 µM kinetin alone produced only shoots (Bhaskaran, S., and Smith, R. H. Crop Sci., 30, 1328-1336 (1990)). Cytokinins, particularly benzyladenine is widely used to proliferate multiple shoots from shoot-tip cultures of many plants.

Somatic embryos of corn arise either directly from the scutellar tissue of the cultured immature zygotic embryos (Vasil, V., Lu, C., Vasil, I. K., Protoplasma 127, 1-8 (1985)) or indirectly from embryogenic calli derived from scutella (Springer, W. D., Green, C. E., Kohn, K. A., Protoplasma 101, 269-281 (1979)). Both pathways of somatic embryogenesis do occur in corn shoot tip cultures (FIGS. 7-9), but the growth regulators which mediate this process vary; 2,4-D triggering the somatic embryogenesis in immature zygotic embryo cultures but both BA and 2,4-D being needed for embryogenesis in shoot-tip cultures. Exogenous cytokinins improve somatic embryogenesis in plants. Somatic embryos were regenerated in clover cultures using BA as sole growth regulator, while both BA and 2,4-D or NAA are required for rye grass, tobacco and corn shoot-tip cultures (Table 1).

De-novo differentiation of shoot apices observed in the shoot-tip cultures as well as on the surface of the scutellar tissue of cultured immature zygotic embryos of corn by Springer et al (Springer, W. D., Green, C. E., Kohn, K. A., Protoplasma 101, 269-281 (1979)) was actually the result of somatic embryogenesis (Vasil, V., Lu, C., Vasil, I. K., Protoplasma 127, 1-8 (1985)). In sorghum and in wheat, both the scutella and the shoot apical meristems produce a "tissue stratum" (compact and organized tissue layer with a smooth epidermis) which, by folding and budding, produces somatic embryos without apparent callusing. Somatic embryos produced in the corn shoot-tip cultures appear also to have developed in such a manner (FIGS. 7, 8). Anomalous embryogenesis does occur in corn and in other cereal cell cultures. Occurrence of both bipolar (somatic embryos) and unipolar (adventitious shoots) structures in close proximity is common in cell cultures of corn, rice and sorghum (Vasil, I. K., J. Plant Physiol. 128, 193-218 (1987); and Bhaskaran, S., Smith, R. H., Crop Sci. 30, 1328-1336 (1990)). The scutellum is a modified leaf, and the leafy nature of the scutellum in the precociously-germinating somatic embryos can be seen in the scanning electron micrographs of the corn cultures (FIGS. 7, 8). Spatial separation of scutella and embryonic axes (FIG. 8) and contiguous formation of multiple coleoptiles (FIG. 7) with or without subtending scutella were frequently observed in embryogenic cultures of other grasses. Somatic embryos do not develop in a controlled-ovular environment like zygotic embryos. Therefore complete organization of somatic embryos is seldom observed in many grasses.

Genotypic differences in plant regeneration in corn cultures can be circumvented by altering the concentration of growth regulators (Vasil, I. K., J. Plant Physiol. 128, 193-218 (1987)) in the culture medium. Likewise shoot tips of corn cultured on 2,4-D alone failed to regenerate plants, but BA alone or in combination with 2,4-D induced regeneration of plants in all 20 corn genotypes tested. The requirement of BA both for shoot formation and for somatic embryogenesis in several corn genotypes indicates that cytokinin may be a key regulator of morphogenesis in shoot-tip cultures of corn. The shoot tip or apices are preferably grown for 12 to 25 weeks in the BS medium with the BA alone or with 2,4-D. The rooted plant is produced in between 12 to 25 weeks or preferably 12 to 25 weeks in the MS medium with the IBA alone or with the BA.

It is intended that the foregoing description be only illustrative of the present invention and that the present invention be limited only by the hereinafter appended claims.

We claim:

1. A method for asexually propagating corn plant tissue in vitro to produce a fertile corn plant which comprises:
   (a) growing isolated immature corn shoot tip or apices plant tissue obtained from a germinated seed in a first MS basal growth medium containing a first growth promoting compound selected from the group consisting of $N^6$-benzyladenine and mixtures of $N^6$-benzyladenine with 2,4-dichlorophenoxyacetic acid wherein the first growth medium contains between 4.5 and 18 µM of the $N^6$-benzyladenine and 0.001 to 2.25 µM of the 2,4-dichlorophenoxyacetic acid in the first growth medium in combination with casein hydrolysate at a concentration which promotes differentiated tissue in the form of multiple shoot formation, calli proliferation or somatic embryos of the plant tissue;
   (b) growing the differentiated tissue in a second MS basal growth medium in the presence of a second growth promoting compound selected from the group consisting of indole-3-butyric acid and mixtures of indole-3-butyric acid with $N^6$-benzyladenine to produce a rooted plane wherein indole-3-butyric acid is present in an amount between about 1.8 and 3.6 µM and the BA is present in an amount between about 2.25 and 9.0 µM in the second growth medium; and
   (c) growing the rooted plant in soil to produce a fertile corn plant.

2. The method of claim 1 wherein the first growth medium contains between about 0.5 and 1 g per liter of casein hydrolysate.

3. The method of any one of claims 1 and 2 wherein step (a) is conducted over a period of about 12 to 15 weeks.

4. The method of any one of claims 1 and 2 wherein step (b) is conducted over a period of about 1 to 6 weeks.

5. The method of claims any one of 1 and 2 wherein step (a) is conducted over a period of between about 12 and 25 weeks and step (b) is conducted over a period of about 1 to 6 weeks.

* * * * *

UNITED STATES PATENT AND TRADEMARK OFFICE
CERTIFICATE OF CORRECTION

PATENT NO. : 5,320,961
DATED : June 14, 1994
INVENTOR(S) : Heng Zhong, et. al.

It is certified that error appears in the above-indentified patent and that said Letters Patent is hereby corrected as shown below:

Title page, after the Title, it is requested that the following be inserted --This application was funded under U.S. Agency For International Development Contract No. USAID DAN4197-A-00-1126-00. The U.S. Government has certain rights under this patent.--

Column 2, line 27, after "showing" and before "scanning" --a-- should be inserted.

Column 3, line 7, "2,25" should read --2.25--.

Column 4, line 9, "Skook", should read --Skoog--.

Column 10, line 42 (Claim 1), "plane" should be --plant--.

Signed and Sealed this

Thirteenth Day of December, 1994

Attest:

BRUCE LEHMAN

Attesting Officer     Commissioner of Patents and Trademarks